United States Patent [19]

Bodicky

[11] 4,333,455
[45] Jun. 8, 1982

[54] INJECTABLE CATHETER AND METHOD OF PLACING SAME

[75] Inventor: Raymond O. Bodicky, St. Louis, Mo.

[73] Assignee: Sherwood Medical Industries Inc., St. Louis, Mo.

[21] Appl. No.: 106,493

[22] Filed: Dec. 26, 1979

[51] Int. Cl.³ ............................................. A61M 5/00
[52] U.S. Cl. ......................... 128/214.4; 128/218 R; 128/348; 221/278; 226/99
[58] Field of Search ................. 128/214, 214.4, 347, 128/348, 218, 221, 262, DIG. 16; 221/278; 226/97

[56] References Cited

U.S. PATENT DOCUMENTS

| | | | |
|---|---|---|---|
| 3,000,380 | 9/1961 | Doherty | 128/214.4 |
| 3,703,174 | 11/1972 | Smith . | |
| 3,757,771 | 9/1973 | Ruegg et al. . | |
| 3,774,605 | 11/1973 | Jewett . | |
| 3,825,001 | 7/1974 | Bennet et al. . | |
| 3,826,256 | 7/1977 | Smith . | |
| 3,835,854 | 9/1974 | Jewett . | |
| 4,037,600 | 7/1977 | Poncy et al. . | |
| 4,191,185 | 3/1980 | Lemieux | 128/214.4 |
| 4,205,675 | 6/1980 | Vaillancourt | 128/348 X |

Primary Examiner—Stephen C. Pellegrino
Attorney, Agent, or Firm—Wegner, McCord, Wood & Dalton

[57] ABSTRACT

A catheter introducer (15) includes a tubular component (20) with a pliable catheter (22) disposed lengthwise therein. The tubular component (20) is connected to an introducer cannula (52) that has been placed in a body passageway (65). Pressurized fluid is forced around and along the catheter (22) in the tubular component (20) to flow the catheter (22) into the body passageway (65). An enlarged proximal end (29) of the catheter (22) seats in a tapered portion (56) of the introducer cannula (52). The proximal portion (56) of the introducer cannula (52) becomes the connector for connecting the catheter (22) to an intravenous unit (70). In a modification, a Y component (32) has a needle (60a) in one leg of the Y for insertion into a body passageway (65) so that, after the needle (60a) is withdrawn, the catheter (22) may be flowed by pressurized fluid through the other leg of the Y component (32) into the body passageway. Additional modifications provide for forming the tubular component in a coil form (220) or in a U-shaped form (420). In all forms of the tubular component (20), the catheter (22) is stored in a configuration wherein no length of catheter (22) contacts any other length of the catheter (22) and the catheter is supported so as not to kink or double over during insertion.

8 Claims, 11 Drawing Figures

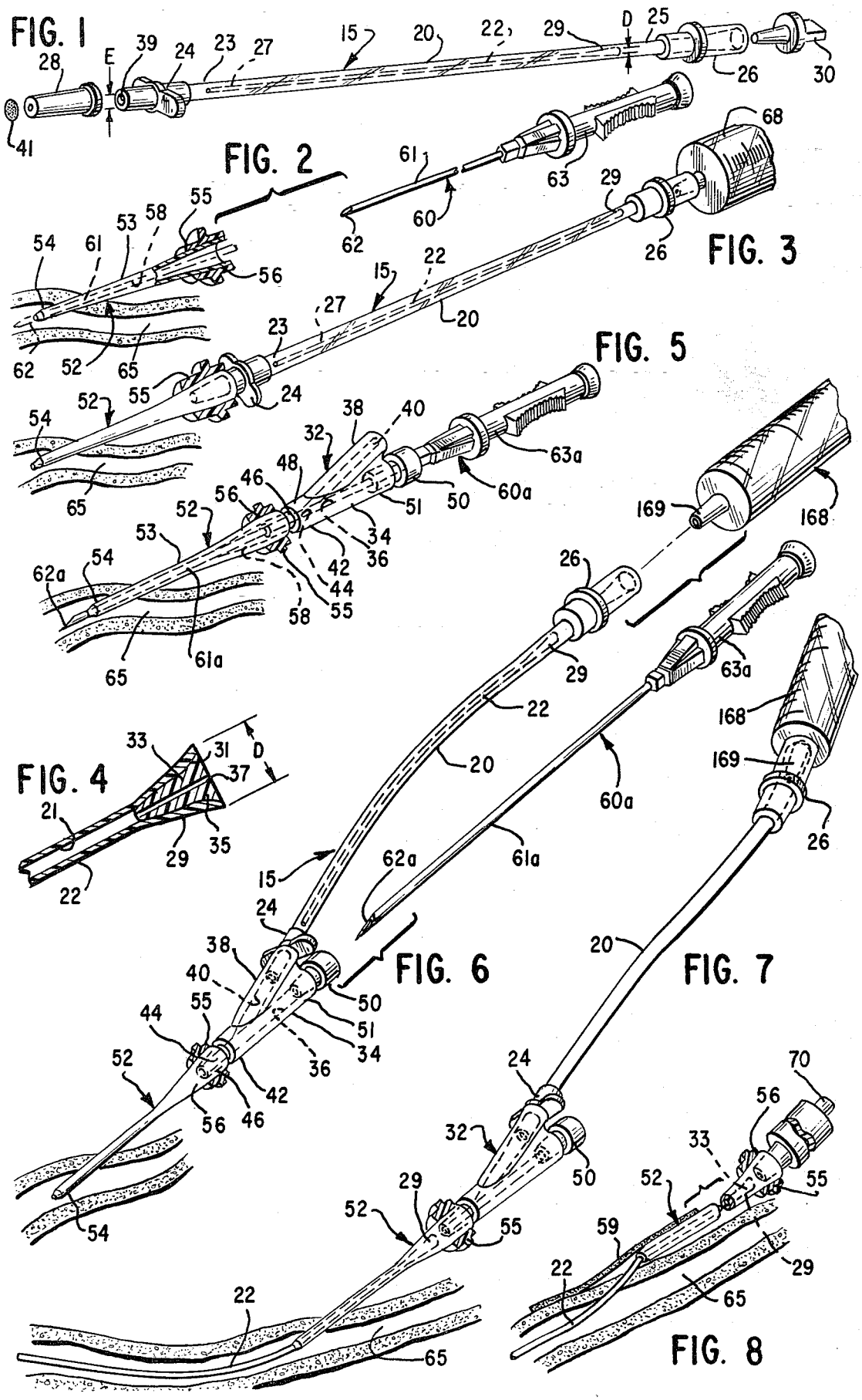

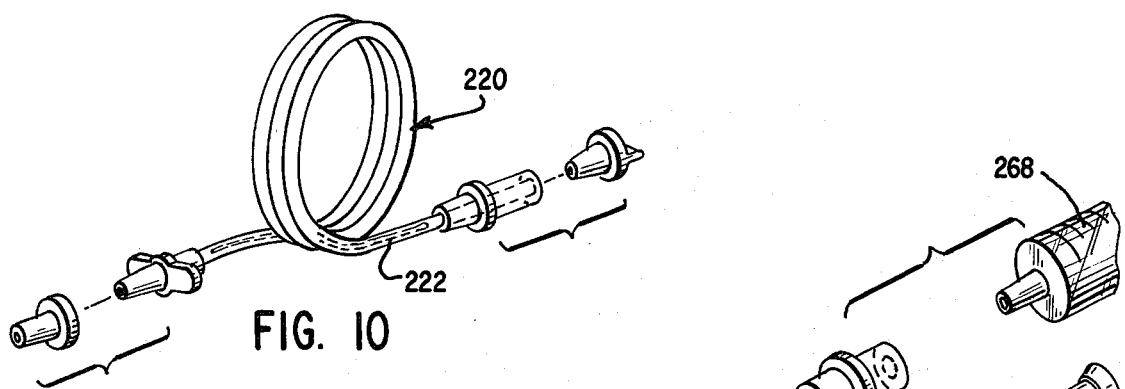
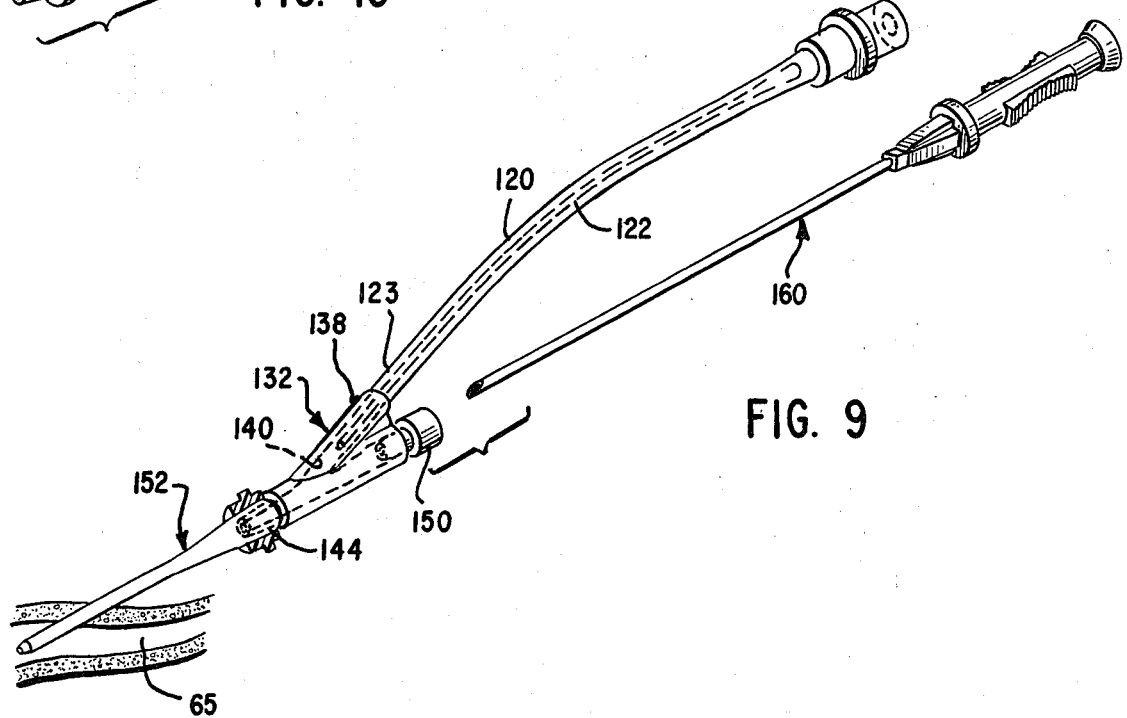
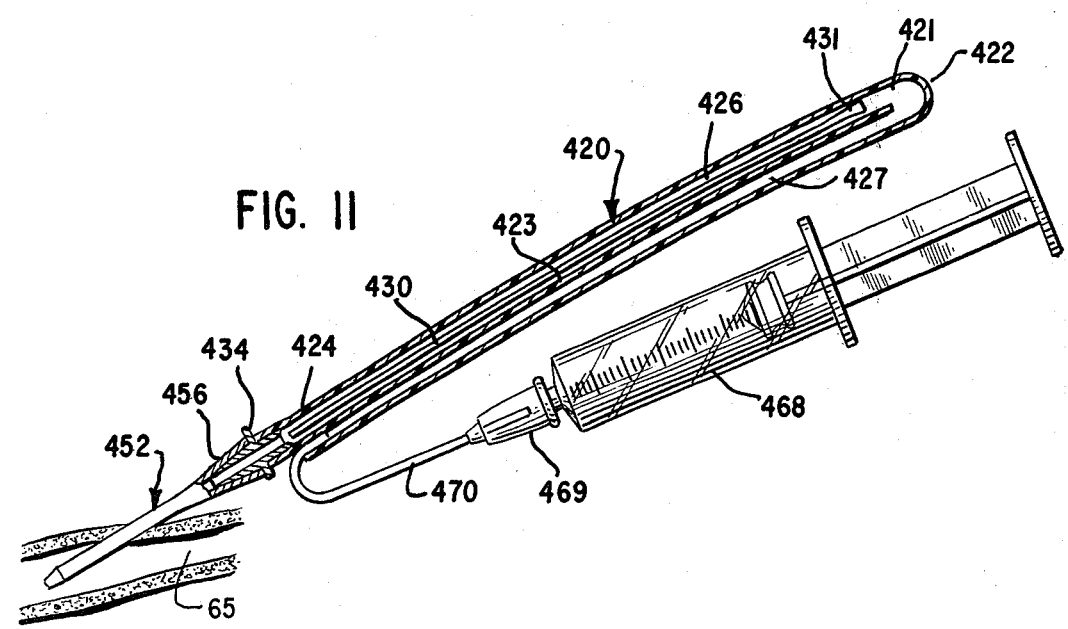

INJECTABLE CATHETER AND METHOD OF PLACING SAME

DESCRIPTION

1. Technical Field

This invention relates to a catheter and, more particularly, to a catheter introducer device using a fluid placement medium and a method of placing said catheter.

2. Background Art

This invention relates to a catheter introducer for inserting a catheter into a passageway, such as a blood vessel. A catheter so inserted is commonly used to inject an intravenous solution or to keep blood vessels free from blockage.

Typical prior devices have required manual manipulation using sheaths and/or gloves to thread the catheter into place. On such device is shown in the Poncy et al U.S. Pat. No. 4,037,600, wherein a catheter is threaded through a V-shaped component after a special needle has been used to form a venipuncture. The catheter is retained in a flexible sleeve and is hand manipulated through the sleeve to thread the catheter into the passageway. The catheter must have some degree of stiffness in order to be threaded into the passageway and around bends and joints in the passageway. The catheter must not be too stiff so as not to cause damage to the passageway as it is manipulated into place.

Other threading devices are shown in the Bennet et al U.S. Pat. No. 3,825,001 and the Jewett U.S. Pat. No. 3,835,854 wherein a plastic sheath ('001) for a chamber ('854) are used to store the catheter prior to and during manipulation of the catheter in place.

All three above-identified patents provide for inserting the catheter at a non-constant rate which increases patient discomfort.

An improved apparatus was provided by the teachings of the Smith U.S. Pat. Nos. 3,703,174 and 3,826,256 wherein a very flexible catheter (wet noodle limpness) is inserted into a passageway by the use of an introducer needle and a fluid placed under pressure behind and between the juncture of the catheter and the needle cannula, which fluid propels the catheter into the passageway for a relatively great distance and at a relatively uniform rate. The catheters are stored in a coiled condition either in or out of a fluid solution such that, even though limp, the catheters have a tendency to stick together and/or to take a set creating insertion problems through the needle and threading problems in the passageway. That is, the tendency for the catheter to want to curl lengthwise causes hangups and blockages in the needle and, in the passageway, tends to curl toward the passageway wall which will slow down or stop the insertion of the catheter. Accordingly, exceptional care must be taken in manufacturing the Smith apparatus and the shelf life of the apparatus must be monitored to assure that catheters that have portions stuck together or have taken a set are removed before use.

The present invention is directed to overcoming one or more of the problems as set forth above.

DISCLOSURE OF INVENTION

This invention relates to a catheter introducer device wherein pressurized fluid is injected into the proximal end of a relatively stiff tubular component containing the catheter, thereby moving the catheter through the tube and attached introducer cannula into a body passageway. In effect, the catheter is flowed into the passageway by the fluid flowing around and along the outer surface of the catheter. The catheter has an enlarged segment at its proximal end which prevents the catheter from being completely injected into the passageway. The enlarged segment may be formed by an extrusion process or by injection molding, or the like, and may have an eyelet inserted in the enlarged segment to prevent collapse thereof and to assist in wedging the catheter in sealing relationship in the introducer cannula. The catheter is stored in the tube in a way that prevents portions of the catheter from sticking together and prevents the catheter from kinking during insertion in a body passageway.

The device further contains a Y component which enables the lumen of the introducer cannula to receive an introducer needle, easing introduction of the introducer cannula into the passageway while also permitting the withdrawal of the needle and introduction of the catheter into the introducer cannula while maintaining a sterile condition. By introducing the catheter and the needle through different forks of the Y component, a sterile seal may be maintained even as the needle is withdrawn from the introducer cannula and is replaced by the catheter.

An improved method is disclosed for introducing a catheter into a body passageway and for connecting an I.V. unit directly to the introducer cannula.

The device permits quick injection of a catheter with relatively little effort, thereby minimizing patient discomfort. Further, the components of the device may be inexpensively made and easily used. The device also permits separate insertion of the needle and catheter into the introducer cannula, thus allowing use of a conventional flashback vent plug with the needle to indicate proper placement in the passageway (i.e., blood vessel) while totally eliminating the problem of the needle point cutting the catheter in the passageway.

BRIEF DESCRIPTION OF DRAWINGS

FIG. 1 is an exploded perspective view of a tubular component with a catheter therein;

FIG. 2 is a view showing an introducer cannula placed in a body passageway with the needle removed from the introducer cannula;

FIG. 3 is a perspective view of one preferred embodiment of the invention showing the tubular component and catheter connected to the introducer cannula;

FIG. 4 is an enlarged partial view of the proximal end portion of the catheter with an eyelet in place therein;

FIG. 5 is a perspective view of an introducer cannula, Y component and needle showing the needle and cannula penetrating into a body passageway, such as a blood vessel;

FIG. 6 is a partially exploded perspective view of the device of FIG. 5 after withdrawal of the needle and prior to injection of the catheter;

FIG. 7 is a perspective view of the device of FIG. 5 after the catheter has been injected into the passageway or vessel;

FIG. 8 is a perspective view showing the catheter as in FIG. 7 with the Y component removed, the introducer cannula backed out of the venipuncture and taped to the skin and an I.V. line connected thereto;

FIG. 9 is an exploded view of a modification wherein the tubular component is attached directly to the Y component;

FIG. 10 is a further modification of the tubular component; and

FIG. 11 is an elevational view partially in section of still another modification of the tube component.

BEST MODE FOR CARRYING OUT THE INVENTION

A catheter introducer device 15, shown in FIG. 3, consists of several separate components which are connected together for use. FIG. 1 shows a tube or tubular component 20 with a catheter 22 disposed lengthwise and freely therein. A distal end 23 of the tubular component 20 has a male luer adapter 24 sealed thereon while the proximal end 25 has a female luer adapter 26 sealed thereon. The tubular component 20 may be made of any flexible material, but is preferably made of a transparent material, such as polyethylene, or the like. The material should be transparent or have an elongate window along the length thereof so that a user of the device can observe the discharge of the catheter 22 from the tubular component 20.

It is preferred that the catheter 22 have a lumen 21 and be made of a silicone rubber material of low reactivity, nontoxic and quite elastic. The catheter 22 has a distal end 27 which either may be rounded and closed with side ports radiating outwardly from the lumen 21 in the distal portion, or may be opened, as shown. The proximal portion 29 of the catheter 22 is flared outwardly (see FIGS. 1 and 4) to form an enlarged segment 31. A fail-safe eyelet 33, preferably made of an appropriate metal, has an outwardly flared end portion 36 and an opening 37 therethrough. The opening 37 of the eyelet 33 has a diameter substantially equal to the diameter of the lumen 21 in the catheter 22. FIG. 4 illustrates a preferred location of the eyelet 33 in the proximal portion 29 of the catheter 22 wherein the flared end portion 35 of the eyelet 33 forms a support for the flared enlarged segment 31 of the catheter 22 to prevent collapse of the segment 31. It should be noted in FIG. 4 that the outer diameter of the flared end portion 35 of the eyelet 33 is within the confines of, and is less than, the largest outside diameter of the enlarged segment 31 of the catheter 22. The outside diameter "D" of the flared enlarged segment 31 FIGS. 1 and 4 is slightly smaller than the inside diameter "E" of the tubular component 20 and 11 of the passageway 39 through the male luer adapter 24 (FIG. 1) for a reason to become apparent hereinafter. The tubular component 20 is shipped and stored as an individual item in the forms of invention shown in FIGS. 1 through 8, 10 and 11, and, therefore, a cap 28 is fit over the male luer adapter 24 and a plug 30 is inserted in the female luer adapter 26 to retain the catheter 22 in a sterile condition in the tube or tubular component 20. A porous sealing strip 41 is provided over one opening in the end of the cap 28, which strip 41 retains the sterility of the contents of the tubular component 20, but permits air to be purged from the tubular component 20 when desired.

FIGS. 2 through 4 and 8 show one preferred form of the invention and the method of using same. In FIG. 2, an introducer cannula 52, of appropriate medical grade material, such as teflon, polypropylene, or the like, is shown and is comprised of an elongate, substantially straight body portion 53 with a tapered distal end portion 54 and an enlarged funnel-shaped proximal portion 56. A lumen 58 is provided lengthwise of the introducer cannula 52. A hub 55 is secured to, or molded on, the enlarged proximal portion 56 to provide a female luer adapter on the proximal portion 56 of the introducer cannula 52. An introducer needle 60 has an elongate portion 61 which passes through the lumen 58 of the introducer cannula 52 with a penetrating point 62 on the distal end extending beyond the tapered distal end portion 54 of the introducer cannula 52. The introducer needle 60 may have a flashback vent plug 63 on the proximal portion thereof. The distal end portion 54 is shown in FIG. 2 placed in a body passageway 65. The close relationship between the internal diameter of the tubular component 20 and the external diameter of the catheter 22 and proximal portion 29, referred to above, provides lateral support for the catheter as it is flowed from the tubular member preventing kinking and sticking together of overlapping portions of the catheter through a venipuncture, which puncture was formed by the point 62 of the needle 60 when the needle (shown in dashed lines) was in place in the introducer cannula 52. When the penetrating point 62 of the introducer needle 60 is in the passageway, in this case a vein or artery, blood will flow through the needle 60 to indicate in the vent plug 63 that the needle 60 and introducer cannula 52 are in the proper position. The needle 60 is now withdrawn from the introducer cannula 52 (as shown in solid lines in FIG. 2).

The tubular component 20 with the catheter 22 therein, has the plug 30 removed and a syringe 68, filled with a saline solution, or the like, is connected to the female luer adapter 26. Expelling fluid from the syringe 68 into the tubular component 20 will purge the air in the tubular component 20 through the strip 41. The strip 41 prevents the catheter 22 from being expelled from the tubular component 20 as the air is being purged. The cap 28 is removed from the male luer adapter 24 of purged tubular component 20 and the needle 60 is withdrawn from the introducer cannula 52 (as shown in solid lines in FIG. 2), whereupon the male luer adapter 24 is seated in the hub 55 in the introducer cannula 52. Expelling the fluid from the syringe 68 into the tubular component 20 will force the fluid around and along the peripheral surfaces of the catheter 22 to flow the catheter 22 through the introducer cannula 52 and into the passageway 65. The enlarged segment 31 of the catheter 22 will pass through the male luer adapter 24, but will seat in the funnel-shaped proximal portion 56 of the introducer cannula 52.

The tubular component 20 and syringe 68 are disconnected from the introducer cannula 52 whereupon the introducer cannula 52 is pulled out of the venipuncture leaving the majority of the length of the catheter 22 in the body passageway 65. As shown in FIG. 8, a male luer adapter of an I.V. unit 70 is connected directly to the hub 55 on the proximal portion 56 of the introducer cannula 52 and the introducer cannula 52 is taped as by tape 59 to the area near the venipuncture. The introducer cannula 52 not only provides the structure for guiding the catheter 22 into the passageway 65, but also has the funnel-shaped proximal portion 56 serving as a locking ferrule for gripping the material of the enlarged segment 31 of the catheter 22 to form a seal therebetween. In addition, the hub 55 on the portion 56 of the introducer cannula 52 serves as a connector for connecting the I.V. unit 70, or the like, directly thereto.

A second preferred form of the invention is shown in FIGS. 5, 6 and 7, wherein a Y-shaped component 32 is provided and has a straight leg 34 with a through passage 36 and a branch leg 38 with a passage 40. The legs 34, 38 merge into a stem 42 with a common passage 44 in line with the straight passage 36. A male luer adapter 46 is integrally formed on the distal end 48 of the stem 42 and a self-sealing plug 50 is attached at the proximal end 51 of the straight leg 34. The introducer cannula 52, as described with respect to FIG. 2, has the proximal portion 56 seated over the male luer adapter 46 on the Y component 32 so that the lumen 58 in the introducer cannula 52 aligns with the passages 44,36 in said Y component 32. An introducer needle 60a, which is substantially the same as introducer needle 60 except that it has a more elongated body portion 61a, has a penetrating point 62a and a flashback vent plug 63a. The elongate body portion 61a is of a length that when the needle 60a is inserted through the sealing plug 50 and the passages 44,36 of the Y component 32 and through the lumen 58 of the introducer cannula 52, the penetrating point 62a will project just beyond the tapered distal end portion 54 of said introducer cannula 52.

As shown in FIG. 5, the penetrating point 62a of the introducer needle 60a is used to make a venipuncture into a passageway 65 in the patient with the distal end portion 54 of the introducer cannula 52 accompanying the needle 60a into the passageway 65. When the penetrating point 62a of the needle 60a is in the passageway 65, in this case a vein or artery, blood will flow through the lumen of the needle 60a and will indicate in the flashback vent plug 63a that the needle 60a and introducer cannula 52 are in the proper position.

The tube or tubular component 20 is then grasped and the plug 30 is removed from the one end thereof. A syringe 168, which has a male luer adapter 169 on the end thereof and which has been filled with a saline solution, or the like, is connected with the female luer adapter 26 on the tubular component 20. The plunger of the syringe 168 is depressed to purge the tubular component 20 of air in the same manner as described with respect to FIG. 3, whereupon the cap 28 is removed and the male luer adapter 24 is connected to the opening in the branch leg 38 of the Y component 32. The introducer needle 60a is now withdrawn from the Y component 32 (FIG. 6). The plunger of the syringe 168 is sharply, but firmly, depressed to expel saline solution into the tubular component 20 whereupon the fluid will flow around and along the catheter 22 to flow the catheter 22 through the tubular component 20, passages 40 and 44 of the Y component 32 and introducer cannula 52 into the passageway 65. The flared proximal portion 29 of the catheter 22 will pass through the opening "E" in the male luer adapter 24 and through the passages 40,44 and will seat in the funnel-shaped proximal portion 56 of the introducer cannula 52. The syringe plunger can then be drawn back slightly to draw blood into the catheter 22 to be sure the catheter is in the passageway and functioning properly. The Y component 32 with the tubular component 20 and syringe 168 still attached is then separated from the introducer cannula 52. The relatively straight and relatively stiff tubular component 20 assures the catheter 22 of a relatively straight storage area and a relatively straight alignment surface for introducing the catheter into the passageway.

Once the catheter 22 is in place, the introducer cannula 52 may be withdrawn from the passageway 65 and placed so that the enlarged proximal portion or segment 29 of the catheter 22 is seated in the introducer cannula 52. The introducer cannula 52 is then taped to the skin, in the same manner as described with respect to FIG. 8, so as to reduce irritation to the area around the venipuncture and to assure that the distal end portion 54 of the cannula 52 does not cut the catheter 22. An I.V. unit 70 may then be connected to the introducer cannula 52 in the manner described with respect to FIGS. 2 through 4.

FIG. 9 shows essentially the same elements as shown and described in FIGS. 5 through 7, with the exception that the distal end 123 of the tubular component 120 is integrally formed with the branch leg 138 of the Y component 132. Using the modification of FIG. 9, the system is purged of air before the introducer needle 160 and introducer cannula 152 are implanted in the passageway 65 of the patient. The purging takes place by depressing the plunger in syringe 268 to force solution through the tubular component 120 through the passageways 140,144 of the Y component 132 and out the introducer cannula 152. Thereafter, the introducer needle 160 is pushed through the plug 150, the Y component 132 and the introducer cannula 152. The introducer needle 160 and introducer cannula 152 are inserted in the passageway 65 and the catheter 122 is injected into the passageway as described above.

FIG. 10 shows another form of tubular component 220. That is, the tubular component 220 is wound in a spiral coil with mild solvent bonding being used to hold adjacent coils together. The coiled configuration permits longer length catheters 222 to be used. The tubular component 220 of FIG. 8 is used to guide a catheter 222 into a passageway as described with respect to FIGS. 2 through 4. Although the catheter 222 is coiled, no length of the catheter is in contact with another length thereof so as to prevent the lengths of catheter from sticking together. In addition, the coils of the tubular component 220 support the catheter 222 preventing kinking of the catheter 222 in said tubular component 220. Fluid expelled from a syringe into the tubular component 220 will flow the catheter 222 out of the tubular component 220 through an introducer cannula and into a passageway.

FIG. 11 shows still a further modification of the invention and, in particular, a tube or tubular component 420 is shown in a configuration with a U-shaped internal chamber 421. The tubular component 420 is closed at the proximal end 422 and has a dividing wall 423 extending from the distal end 424 to just short of the closed proximal end 422 so that the chamber 421 has two cavities or branches 426,427 joined at the end remote from the distal end 424. A catheter 430, of the same type and description as set out in FIGS. 1 through 10, is positioned in branch 426 with the flared proximal end 431 located in the vicinity of the proximal end 422 of the tubular component 420. The branch 426 of the tubular component 420 has a male luer adapter 434 which is adapted to be seated in the flared end portion 456 of the introducer cannula 452.

A syringe 468 is connected to a female connector 469 on the end of a flexible conduit 470. The conduit 470 is connected into an end of the branch 427 of the tubular component 420. The system is purged of air by depressing the plunger of the syringe 468 until the fluid of the syringe 468 flows out the male luer adapter 434. The introducer cannula 452 is inserted in the passageway 65 by means of an introducer needle, similar to introducer needle 60 described above, positioned in the introducer cannula 452. After the needle is removed from the introducer cannula 452, the tubular component 420 is connected to the introducer cannula 452. Depressing the plunger of the syringe 468 advances the catheter 430 from the branch 426 and into the introducer cannula 452 and passageway 65. The enlarged proximal portion 431 on the catheter 430 seats in the introducer cannula 452 whereupon the tubular component 420 is disconnected from the cannula. The introducer cannula 452 is pulled out of the venipuncture, pulling a portion of the catheter 430 with it. The introducer cannula 452 is then taped to the skin near the venipuncture whereupon an intravenous tube or I.V. unit is attached as described above.

One advantage to the tubular component 420 of FIG. 11 is that the technician can hold, with one hand, both the introducer cannula 452 and the tubular component 420. The other hand is free to operate the syringe 468.

Other aspects, objects and advantages of this invention can be obtained from a study of the drawings, the disclosure and the appended claims.

I claim:

1. A catheter placement device for propelling an elongate flexible and elastic catheter into a body passageway;
    an elongate tubular means having a hollow internal cavity throughout the length thereof, said tubular means being substantially straight and having a longitudinal axis throughout the length thereof, an enlarged proximal portion on said flexible and elastic catheter; said flexible and elastic catheter being disposed completely within said tubular means and having a longitudinal axis lying along a longitudinal axis of said tubular means; said tubular means having an internal diameter slightly greater than the external diameter of the elastic catheter and of the enlarged proximal portion of said elastic catheter to support the catheter along its length;
    an introducer cannula having one end portion insertable into said body passageway;
    means for connecting a distal end of said tubular means with said introducer cannula; and
    dispensing means removably connected to a proximal end of said tubular means for selectively expelling fluid into said tubular means for propelling said flexible and elastic catheter along the axis of said tubular means and out of the distal end of said tubular means and partially through said introducer cannula and partially into said body passageway.

2. A catheter placement device as claimed in claim 1 wherein said elongate tubular means is a sleeve made of a transparent inert plastic material.

3. A catheter placement device as claimed in claim 2 wherein said means for connecting said tubular means with said introducer cannula is a male luer adapter sealed on the distal end of said sleeve, and wherein a female luer adapter is sealed on the proximal end of said introducer cannula.

4. A catheter placement device as claimed in claim 1 wherein said dispensing means is a syringe.

5. A catheter placement device as claimed in claim 1 wherein said tubular means is divided into two parallel cavities communicating with each other at the proximal end thereof, one of said cavities containing said flexible catheter, a distal end of said catheter aligning with said means for connecting said tubular means to said introducer cannula, the other of said cavities being connected to said dispensing means whereby fluid expelled by said dispensing means propels said catheter into said body passageway through said introducer cannula.

6. A catheter placement device as claimed in claim 1 wherein said flexible catheter has a funnel-shaped proximal end portion and wherein an eyelet is seated in said funnel-shaped portion to prevent collapse of said funnel-shaped portion.

7. A catheter introducer, comprising:
    a stiff tube having a longitudinal axis, a flexible catheter having a longitudinal axis disposed lengthwise along the axis of said tube; said stiff tube having an internal diameter slightly larger than the external diameter of said catheter so as to provide lateral support for said catheter;
    means connecting the distal end of said tube to a body passageway; and
    means for injecting liquid into the proximal end of said tube for propelling said flexible catheter from said tube and into said body passageway.

8. The catheter introducer of claim 7 wherein said catheter has an enlarged segment maintained by an eyelet seated in said proximal portion of the catheter, said internal diameter of said tube being slightly larger than the external diameter of said enlarged segment.

* * * * *